US00PP15682P2

(12) United States Plant Patent
Evison et al.

(10) Patent No.: US PP15,682 P2
(45) Date of Patent: Mar. 22, 2005

(54) ***CLEMATIS* PLANT NAMED 'EVIPO012'**

(50) Latin Name: *Clematis viticella*
Varietal Denomination: EVIpo012

(75) Inventors: Raymond Evison, St. Sampson (GB); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/440,060

(22) Filed: May 15, 2003

(51) Int. Cl.[7] ..... A01H 5/00
(52) U.S. Cl. ..... Plt./228
(58) Field of Search ..... Plt./228

*Primary Examiner*—Kent Bell

(57) ABSTRACT

A new *Clematis* cultivar which is well suited to propagation from softwood cuttings in glasshouses. The variety has a tall growth habit, profust, Red-Purple flowers, and continuous summer flowering. This new and distinct variety has shown to be uniform and stable in the resulting generations from propagation.

1 Drawing Sheet

Botanical classification: Genus: *Clematis*. Species: *viticella*.

SUMMARY OF THE INVENTION

The present invention constitutes a new and distinct variety of *Clematis* which originated from a chance pollination between the female seed parent, an unnamed seedling, and an unknown pollen parent plant. The new variety is named 'EVIpo012'.

The main characteristic that distinguishes 'EVIpo012' from the seed parent variety is that the unnamed seed parent has a Violet Blue flower color. The same of 'EVIpo012' is Red Purple Group 78C.

The objective of the cultivation of this *Clematis* variety for commercial nursery culture was to create a new and distinct variety with unique qualities, such as:

1. Non clinging habit;
2. A profusion of semi-nodding, light purple flowers;
3. Summer flowering;
4. Well-suited to garden situtations;
5. Very winter hardy in Zones 3 to 9.

These qualities required improvement in *Clematis* varieties that were in commercial cultivation and the objectives have been substantially achieved in the new variety, as evidenced by the unique combination of characteristics that are present in 'EVIpo012' which distinguish it from all other varieties of which we are aware.

The seeds were germinated and evaluations were conducted of the resulting *Clematis* plants in a controlled environment.

'EVIpo012' was selected by Raymond J. Evison and Mogens N. Olesen in their *Clematis* development program in Domarie Vineries Les Sauvagees, St. Sampsons, Guernsey, Channel Islands, United Kingdom in July, 1998.

Asexual reproduction of EVIpo012 by cuttings was first done by Raymond J. Evison and Mogens N. Olesen in Domarie Vineries Les Sauvagees, St. Sampsons, Guernsey, Channel Islands, United Kingdom in August, 1998. This initial and subsequent propagations have demonstrated that the characteristics of 'EVIpo012' are true to type and are transmitted from one generation to the next.

BRIEF DESCRIPTION OF THE DRAWING

The accompanying color illustration show as true as is reasonably possible to obtain in color photographs of this type:

1.1 Stem and leaves;

1.2 Compound leaf and leaflet, upper side;

1.3 Stem, leaves, but at ¼ opening, bud closed;

1.4 Bloom, upper side;

1.5 Bloom, lower side.

DETAILED DESCRIPTION OF THE VARIETY

The following is a detailed description of 'EVIpo012', as observed in its growth throughout the flowering period in glasshouses at Domarie Vineries Les Sauvagees, St. Sampons, Guernsey, Channel Islands, United Kingdom. Observed plants are 2 years of age, and were cultivated in 2 liter pots. Certain phenotypical characteristics of the variety may vary under different environmental, cultural, agronomic, seasonal, and climatic conditions. Color references are made using The Royal Horticultural Society (London, England) Colour Chart, 1995.

For a comparison, the nearest existing *Clematis* variety is 'Alionushka', a non-patented *Clematis* variety. Chart 1 details several physical characteristics of 'EVIpo012' and the comparison variety.

CHART 1

| | 'EVIpo012' | 'Alionushka' |
|---|---|---|
| Tepal length | 40 to 50 mm. | 70 mm. |
| Flower form | Open campanulate. | More elongated, closed camapanulate. |
| Flower color | Purple Group N78C. | Purple Group 78A. |
| Bracts | Small to medium bracts on non-terminal flowers. | Large bracts on non-terminal flowers. |

FLOWER AND FLOWER BUD

Blooming habit: Recurrent in summer. Flowering months are normally late May, June, July, August, and September.

Flower bud:

*Size.*—15 to 20 mm in length. 10 to 12 mm in diameter.

*Bud form.*—Ovoid.

*Bud color.*—Red-Purple Group 72A.

*Tepals.*—Red-Purple Group 78A.

*Peduncle.*—Surface: Smooth. Length: 120 to 180 mm average length. Color: Green Group 137A. Strength: Semi-nodding.

*Receptacle.*—No receptacle observed.

*Borne.*—Compound dichasial cymes.

Flower bloom:

*Size.*—60 to 80 mm diameter on average. Typical bloom depth is 30 to 50 mm.

*Form.*—Campanulate, with tepals slightly reflexed.

*Color.*—Tepal color upon opening: Upper surface: Purple Group N78C. Lower surface: Purple Group N78C. Tepal color after opening: Upper surface: Purple Group N78C. Lower surface: Purple Group N78C. Lower margins of tepal are lighter in color, Purple Group N78D. As flower fades, 3 longitudinal veins retain their color, Purple Group N78C, while the remainder of the tepal surfaces fade.

*Variations.*—None.

*Fragrance.*—None.

*Lasting quality on plant.*—Short; 7 to 10 days on the plant, 2 to 4 days as a cut flower.

Tepals:

*Quantity.*—4 tepals.

*Shape.*—Elliptic.

*Length.*—40 to 50 mm.

*Width.*—20 mm.

*Cross section.*—Slightly reflexed.

*Margin.*—Entire. Normally undulates 3 to 34 times along margin length.

*Tepal apex.*—Narrowly acute.

*Tepal base.*—Rounded.

*Recurvature of tip.*—Outer tepals occasionally recurved.

*Persistence.*—Tepals drop off cleanly.

*Arrangement.*—Tepals are arranged regularly.

Reproductive organs:

*Pollen.*—Quantity: Small amount.

*Anthers.*—Size 3 to 5 mm. Pollen: Yellow Group 13C. Arrangement: Regular.

*Filaments.*—Size: 5 to 10 mm. Color: Yellow Group 19D.

*Styles.*—Color: Varies between Green Group 136D and Yellow Group 11D.

*Pistils.*—Quantity: 40 to 60.

*Seed.*—Quantity: 30 to 40 per seed head. Color: Green Group 143C, ripening to Greyed-Orange Group 166C. Shape: Rounded to tear shaped. Size: 4 to 5 mm diameter by 15 to 25 mm in length.

PLANT

Plant form: Upright.

Plant growth: Medium vigor.

Height: Seasons growth attains meters 1.5 to 2 meters. Spread is 0.5 meters.

Hardiness: Trials to date show the variety hardy in USDA Zones 3 to 9.

Stems:

*Color.*—Young wood: Green Group 137C. Older wood: Greyed-Orange Group 165C.

*Internodes.*—Cylindrical. Typical and observed length 90 mm.

*Petioles.*—Size: On compound pinnate leaves, 0 to 50 mm in length. Color: Green Group 137C. Clasping: None.

*Bark.*—Young wood: Smooth. Older wood: Smooth.

Plant foliage: Deciduous. Simple elliptic leaves or compound leaves consisting of 7 elliptic leaflets arranged in pinnate form.

*Foliage size.*—Average terminal leaflet size is 30 to 40 mm long and 15 to 20 mm wide. Average compound leaf size is 150 mm long by 120 mm wide.

*Abundance.*—Average.

*Color of mature leaflets.*—Upper side: Green Group 137A. Lower side: Green Group 137C.

Plant leaves and leaflets:

*Stipules.*—Absent.

*Petiole.*—Color: Green Group 137C. Length: 0 to 50 mm. Underneath:

*Petioloule.*—Length: 0 to 15 mm. Color: Green Group 137B. Without prickles.

*Leaf edge.*—Margins of terminal leaflet and simple leaves are entire.

*Leaflet and simple leaf shapes.*—Base: Rounded to acute. Apex: Acute.

*Texture.*—Upper side: Glabrous. Lower side: Veined.

*Surface.*—Matte finish.

*Thickness.*—Thin.

Disease resistance: Subject to any disease that normally attacks the species, however the variety is more tolerant to Botrytis and *Clematis* Wilt than all other *Clematis* known to us.

It is claimed:

1. A new and distinct variety of *Clematis* plant named 'Evipo012', as illustrated and described herein as a distinct and novel *clematis* variety due to its abundant red-purple flowers with good keepability, attractive long lasting foliage and compact growth, year round flowering under greenhouse conditions, suitability for production from softwood cuttings in pots, durable flowers and foliage which make the variety suitable for distribution in the floral industry.

* * * * *

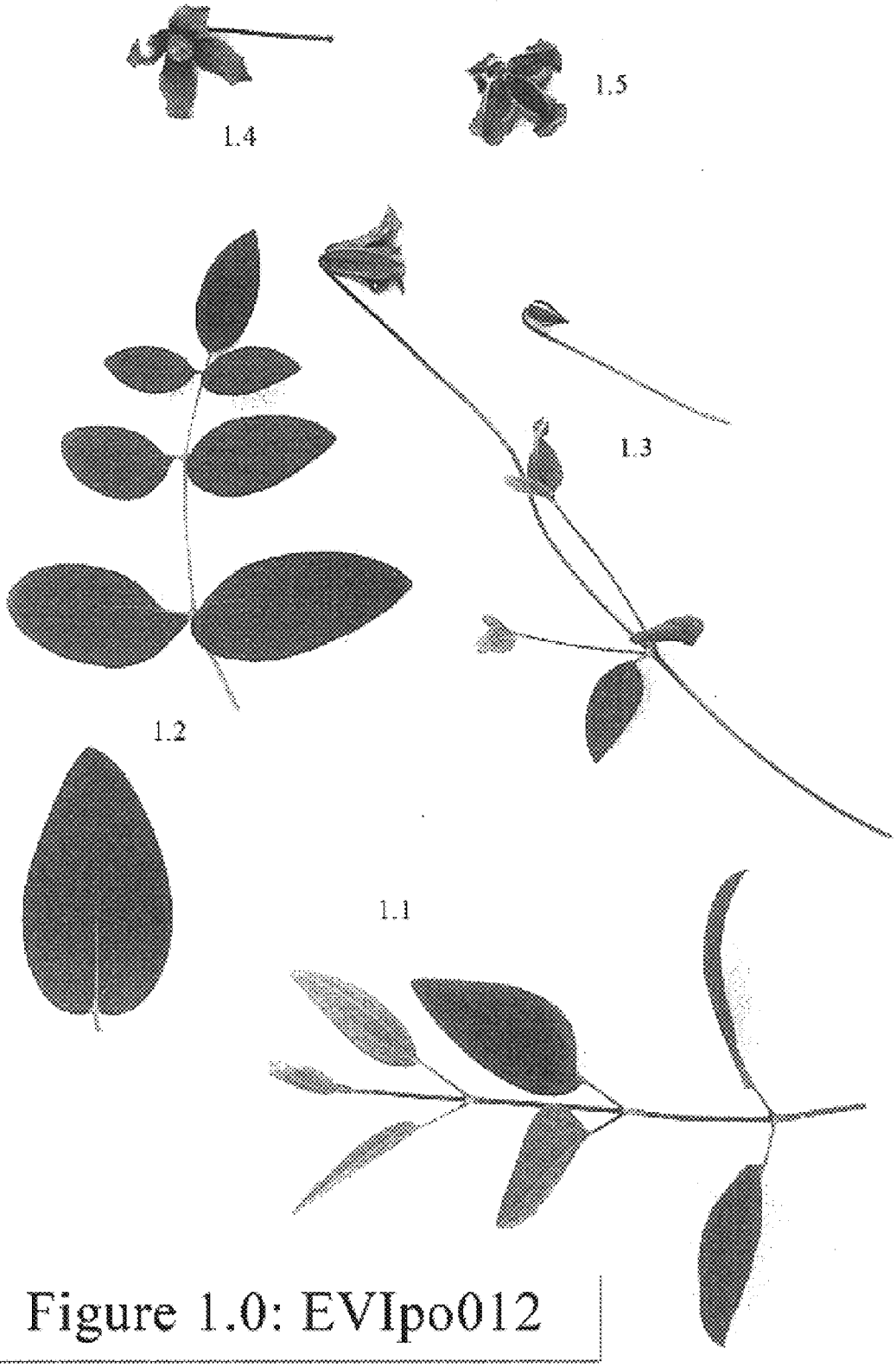
Figure 1.0: EVIpo012